United States Patent [19]

Norton

[11] 4,132,711

[45] Jan. 2, 1979

[54] PROCESS FOR PREPARING NITRILES

[75] Inventor: Richard V. Norton, Wilmington, Del.

[73] Assignee: Suntech, Inc., Wayne, Pa.

[21] Appl. No.: 772,415

[22] Filed: Feb. 28, 1977

[51] Int. Cl.$^2$ .................. C07C 120/00; C07D 213/84
[52] U.S. Cl. ............................ 546/286; 260/326 R; 260/326 N; 260/329 R; 260/346.11; 260/465 R; 260/465 B; 260/465 F; 260/465 H; 260/465.1; 260/465.8 R
[58] Field of Search ........... 260/465 B, 465 R, 465 H, 260/465.1, 465.2, 465.8 R, 294.9

[56] References Cited

U.S. PATENT DOCUMENTS

| | | | |
|---|---|---|---|
| 2,795,599 | 6/1957 | Toland, Jr. | 260/465 R |
| 2,901,504 | 8/1959 | Aries | 260/465 B |
| 3,776,937 | 12/1973 | Gelbein | 260/465 B |

FOREIGN PATENT DOCUMENTS 1181283  2/1970  United Kingdom.

OTHER PUBLICATIONS

Toland et al., J. Org. Chem., vol. 23, pp. 1350–1351, (1958).

*Primary Examiner*—Dolph H. Torrence
*Attorney, Agent, or Firm*—J. Edward Hess; Donald R. Johnson; Paul Lipsitz

[57] ABSTRACT

A process for the preparation of aromatic nitriles which comprises reacting an organic carboxylic acid with an aromatic o-dinitrile whereby the nitrile of the acid is obtained with cyclic imide by-product and the imide by-product is converted to dinitrile and recycled to the reaction.

8 Claims, No Drawings

PROCESS FOR PREPARING NITRILES

This invention relates to a process for the preparation of aromatic nitriles by the reaction of aromatic acids with aromatic o-dinitriles and the by-product aromatic imide that is formed is converted to a dinitrile and recycled.

It is known in the art that an interchange reaction between an acid and a nitrile can occur. Thus, for example, Toland in U.S. Pat. No. 2,795,599 discloses the reaction between toluic acid and p-cyanotoluene. Toland and Ferstanding (J. Org. Chem. 23 1350; 1958) studied the exchange between an aromatic nitrile and an aromatic acid and postulated the formation of an equilibrium in which an imide intermediate was formed; the equilibrium being displaced by distilling out of the reaction mixture the low boiling nitrile product. The reaction was illustrated as follows:

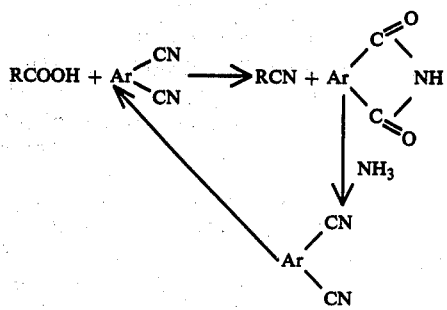

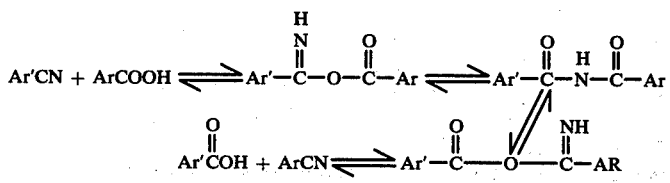

Aliphatic dinitriles have also been reacted with acids. D. A. Klein (J. Org. Chem. 36 3051, 1971) reported that short chain dinitriles such as succinonitrile, glutaronitrile and α-methylglutaronitrile, reacted with an acid to form a cyclic imide. The reaction scheme follows:

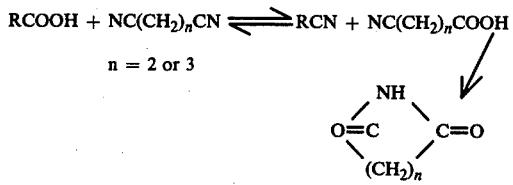

The cyclic aliphatic imide formed in the above reaction may be converted by reaction with ammonia to a dinitrile. However, the severe amination conditions degrade both the reactant and the product and therefore the yield of aliphatic dinitrile is very low and making it unavailable for recycle. Accordingly, it is not economically feasible to effect a continuous, cyclic system where the imide can be recycled by conversion to the aliphatic dinitrile starting material.

It has now been found however, that a recycle system for the preparation of an organic nitrile may be carried out economically by reacting at a temperature of from about 100° to about 300° C. (preferably from about 200° to about 300° C.), a carboxylic acid with an aromatic o-dinitrile to obtain product nitrile and the by-product cyclic imide also obtained is converted by reaction with ammonia to the starting o-dinitrile for recycle.

The reaction process may be indicated as follows:

The starting carboxylic acid may be designated by the formula R-COOH where R is an aliphatic or aromatic group and which will include the "super-aromatic" groups characterized by heterocyclic moeities; i.e. those derived from pyridine, furan, thiophene, and the like. Preferably, the aromatic groups will be of the benzene and naphthalene series, most preferably it will be a benzene group. The R group may be substituted by substituents inert to the reaction and are exemplified by halogen, alkyl, alkoxy, and cyano. Aliphatic R groups include those containing from 1 to about 18 carbon atoms and will be exemplified by methyl, ethyl, butyl, hexyl, dodecyl, lauryl, stearyl and the like. The R-COOH acid may also be a diacid such as adipic, succinic and the like. Preferably, acids of the benzene and naphthalene series will be used such as benzoic acid, toluic acid, 1- and 2-naphthoic acid, adipic and like acids.

The aromatic o-dinitrile may be designated as Ar(CN)$_2$ where Ar is an aromatic group of the benzene and naphthalene series. The aromatic ring may be substituted with groups inert to the reaction and these are exemplified by alkyl, alkoxy, halo, cyano and the like. Preferred species are phthalonitrile, 1,2- or 1,10-dicyano-naphthalene, pyromellitonitrile, and the like.

The reaction is, as indicated, carried out at an elevated temperature of from about 100° to about 300° C. and preferably 200° to 300° C. Temperatures of from about 200° to about 250° C. are used when a protonic catalyst is used (e.g. $H_2SO_4$, $H_3PO_4$, a Lewis acid salt with a trace of water, etc.) and the higher temperature is employed in the absence of catalyst.

The cyclic aromatic imide by-product is readily converted back to the dinitrile in very high yield by reaction with ammonia. Such reactions are known and are disclosed in U.S. Pat. No. 2,901,504, and such disclosure is hereby incorporated by reference. The aromatic dinitrile product is readily recycled as starting material for reaction with aromatic acid and in this way a very efficient over-all process is obtained.

In order to further illustrate the invention, the following examples are given:

EXAMPLES

Example 1. Benzoic acid (12.2g) was mixed with phthalonitrile (12.8g) and placed into a flask with the stopper sealed in place. The system was heated to 250° C. for 6 hours, cooled to room temperature, opened (no pressure buildup) and extracted with benzene.

Distillation of the benzene gave an essentially quantitative yield of benzonitrile. The phthalimide pot residue was recrystallized and recovered in near quantitative yield.

Example 2. Nicotinic acid (11.4g) was treated with phthalonitrile as in Example 1, and 2-cyanopyridine was isolated in greater than 90% yield.

Example 3. Terephthalic acid (16.6g) was mixed with phthalonitrile (51.2g) and heated at 270° C. for 8 hours in a sealed tube. After opening the of tube and extraction with isopropanol followed by recrystallization from benzene, terephthalonitrile and phthalimide was isolated in over 90% yield.

Example 4. Benzoic acid was allowed to react with pyromellitonitrile at 250° C. and after extraction with chloroform/pet ether benzonitrile was isolated in over 80% yield.

Pyromellitimide was shown to be the other product, which was contaminated with 4,5-dicyanophthalimide.

Example 5. A 1 inch tubular stainless steel column was packed with phosphoric acid treated alumina spheres (⅛ inch Dia.) to a depth of 13 inches. A mixture of phthalimide and ammonia in a 1:4 molar ratio was passed over the catalyst at 400° C. to effect dehydration to phthalonitrile.

A conversion of phthalimide to phthalonitrile was effected in over 90%.

Example 6. In the manner of the above example glutarimide and ammonia were reacted over an alumina/acid catalyst at 400° C. The yield of dinitrile was less than 40% and was accompanied by a large HCN make, therefore making the aliphatic dinitriles quite impractical for process development.

Example 7. Adipic acid (0.1 mole) was mixed with phthalonitrile (0.4 moles) and the powdered mixture finely and intimately ground with a mortar and pestle in the presence of one drop of phosphoric acid. The mixture was then heated at 200° C. and extracted with chloroform to obtain adiponitrile (0.075 moles) in 75% yield.

The invention claimed is:

1. A process for the preparation of aliphatic or aromatic nitriles which comprises reacting an organic carboxylic acid of the formula R-COOH where R is an aliphatic or aromatic group with an aromatic o-dinitrile of the formula $Ar(CN)_2$ where Ar is an aromatic group of the benzene and naphthalene series at a temperature of from about 100° to about 300° C. whereby the nitrile of the acid is obtained with cyclic imide by-product, and imide by-product is converted to dinitrile by ammonolysis and said dinitrile is recycled.

2. The process of claim 1 where the o-dinitrile is phthalonitrile.

3. The process of claim 2 where the acid is benzoic acid.

4. The process of claim 2 where the acid is nicotinic acid.

5. The process of claim 1 where the acid is benzoic and the dinitrile is pyromellitonitrile.

6. The process of claim 1 where the acid is an aliphatic acid containing from one to eighteen carbon atoms.

7. The process of claim 6 where the dinitrile is phthalonitrile.

8. The process of claim 7 where the acid is adipic acid.

* * * * *